United States Patent
Scherer et al.

(10) Patent No.: US 6,945,389 B2
(45) Date of Patent: Sep. 20, 2005

(54) CONTACT LENS CONTAINER

(75) Inventors: Anton Scherer, Frammersbach (DE); Klaus Oswald, Riedstadt (DE)

(73) Assignee: Novartis AG, Basel (CH)

( * ) Notice: Subject to any disclaimer, the term of this patent is extended or adjusted under 35 U.S.C. 154(b) by 208 days.

(21) Appl. No.: 10/191,613

(22) Filed: Jul. 9, 2002

(65) Prior Publication Data

US 2003/0066764 A1 Apr. 10, 2003

(30) Foreign Application Priority Data

Oct. 7, 2001 (EP) .......................... 01116817

(51) Int. Cl.⁷ .............................. A45C 11/04
(52) U.S. Cl. .................. 206/5.1; 206/205; 422/113; 422/301; 134/901; 215/260
(58) Field of Search .............. 206/5.1, 205, 1.5; 134/901; 422/113, 301, 297, 300; 215/260, 271, 270, 276

(56) References Cited

U.S. PATENT DOCUMENTS

| | | | |
|---|---|---|---|
| 4,036,386 A | * 7/1977 | Nishioka et al. | 215/260 |
| 4,089,434 A | 5/1978 | Tagalakis et al. | 215/260 |
| 4,637,919 A | * 1/1987 | Ryder et al. | 422/300 |
| 4,750,610 A | 6/1988 | Ryder | 206/5.1 |
| 4,993,572 A | * 2/1991 | Ochs | 215/260 |
| 4,996,027 A | 2/1991 | Kanner | 422/113 |
| 5,250,266 A | 10/1993 | Kanner | 422/113 |
| 5,366,078 A | * 11/1994 | Braun | 206/5.1 |
| 5,558,846 A | * 9/1996 | Alvord et al. | 422/301 |

FOREIGN PATENT DOCUMENTS

| | | |
|---|---|---|
| EP | 0 476 937 B1 | 8/1995 |
| TW | 179950 | 10/1991 |
| WO | WO 99/21774 | 5/1999 |

\* cited by examiner

Primary Examiner—Jila M. Mohandesi
(74) Attorney, Agent, or Firm—Jian Zhou; Robert J. GOrman; R. Scott Meece

(57) ABSTRACT

A contact lens container (1) includes a container (2) for receiving a cleaning and/or disinfecting liquid, as well as a cap (3), which can be screwed onto the container (2) by a thread (20,30). In the cap (3) a sealing washer (4) made of a water-tight and gas-tight material is provided, which is arranged on the inside of the cap (3) on the bottom (33) of the cap and extends to the side wall (32) of the cap (3), so that when the cap (3) is screwed on to the container (2), the sealing washer (4) is enclosed between the container edge (23) and the bottom (33) of the cap and the inside of the container has a water-tight seal. The cap (3) in the area in which the sealing washer (4) is enclosed between the container edge (23) and the bottom (33) of the cap is designed such that a cavity (34) is formed between the sealing washer (4) and the bottom (33) of the cap, so that, when there is excess pressure in the container (2), the sealing washer (4) is deformed into this cavity (34) and gas can escape from the inside of the container through the thread (20,30) out of the container (2). The sealing washer (4) is equipped with a sealing lip (42) at its border with the side wall (32) of the cap (3), the lip being designed such that, when the sealing washer (4) is deformed into the cavity (34), a water-tight seal is ensured with the side wall (32) of the cap (3).

15 Claims, 6 Drawing Sheets

CONTACT LENS CONTAINER

Figure 1:
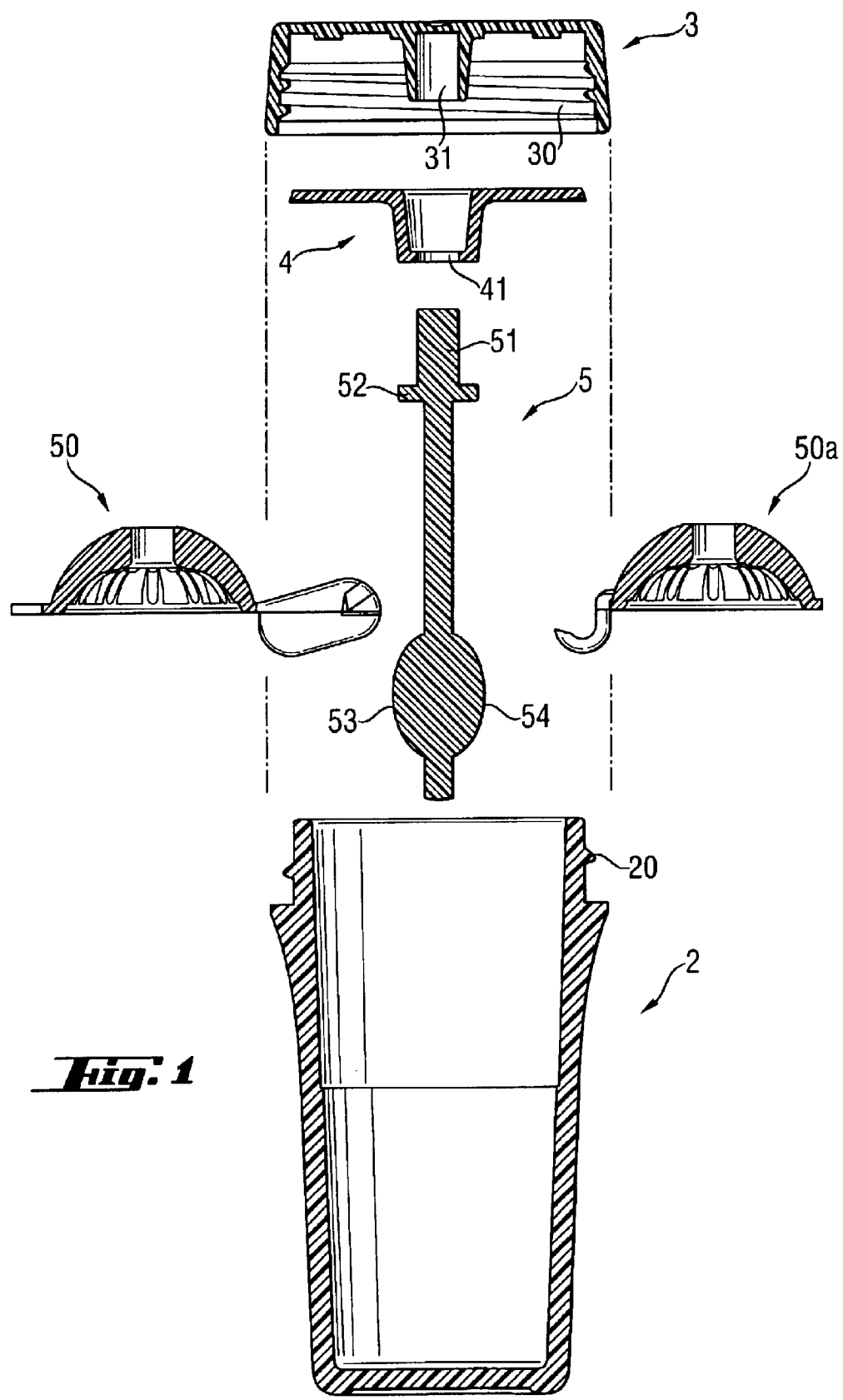

The invention relates to a contact lens container in accordance with the preamble of the independent patent claim.

Contact lens containers have been available commercially for many years in numerous variants. When cleaning and/or disinfecting contact lenses, in some care systems a hydrogen peroxide solution is used, wherein the contact lenses to be cleaned and/or disinfected have to come into contact with the hydrogen peroxide solution for a certain period of time, in order that cleaning and/or disinfecting of the contact lenses can take place to a satisfactory extent. During the duration of the cleaning or disinfecting process, the hydrogen peroxide ($H_2O_2$) in the hydrogen peroxide solution is broken down into water ($H_2O$) and oxygen ($O_2$), e.g. with the aid of catalase tablets which give a delayed release of the catalase which initiates and accelerates the decomposition process. After completion of the decomposition process, cleaning and/or disinfecting is finished and the contact lenses may be removed from the container and inserted into the eye either directly or after treating with a rinsing solution.

The contact lens containers typically comprise closable baskets, into which the contact lenses to be cleaned are placed and then the baskets are closed. The baskets are provided on a contact lens holder, which in turn is normally connected to the cap of a contact lens container. Before the cap is in place, the hydrogen peroxide solution is filled into the container. The catalase tablet, which gives delayed release of catalase, can be added either now or even before adding the hydrogen peroxide solution. Finally, by screwing the cap onto the container, the container is closed with a water-tight seal, and the contact lenses on the contact lens holder are immersed into the hydrogen peroxide solution, so that the cleaning and/or disinfecting process (contact of the contact lenses with the hydrogen peroxide solution) and the subsequent decomposition of the hydrogen peroxide can take their course. The oxygen being produced when the hydrogen peroxide breaks down must be able to escape from the container without any undue excess pressure building up in the container.

As already mentioned at the beginning, contact lens containers of this kind are already available commercially. The seal which prevents leakage of the liquid is provided, for example, with the aid of a sealing washer, which is placed in the cap and when the cap is screwed onto the container is clamped between the container and the cap, thus preventing leakage from the container. In order to allow the oxygen being produced during decomposition of the hydrogen peroxide to escape, there are basically three fundamental constructional arrangements.

The first arrangement provides vents in the cap, which extend from a cavity behind the seal right through the cap. In the sealing washer, openings (e.g. slits) are provided, which are essentially water-tight and through which the oxygen being formed during decomposition of the hydrogen peroxide can escape from the inside of the container to the outside. So that this can take place, the sealing washer must be able to reversibly deform at least in the area of the slit, for which reason certain cavities are provided in the area of these openings between the sealing washer and the cap.

The second arrangement similarly provides vents in the cap, which extend from a cavity behind a sealing membrane arranged in the cap, right through the cap. The sealing membrane is permeable to gas, but not to liquids, so that the oxygen can escape but no liquid can pass through the membrane into the cavity. Of course, if the contact lens container is not in its normal position (but is e.g. is lying down or has fallen, etc.) and, during the cleaning and/or disinfecting process, the oxygen being formed and the liquid simultaneously press against the sealing membrane, there is the danger even here that residues of liquid may pass through the sealing membrane into the cavity behind the sealing membrane. In addition, the sealing membrane is welded into the cap, which, from a manufacturing point of view, is linked with a very substantial cost.

The third arrangement does not provide any ventilation via vents in the cap, but ventilation takes place via the thread between the container and the cap. To do this, the sealing washer must be able to reversibly deform at its periphery, so that the oxygen can pass out from the inside of the container through the pitch of the thread. In this case also, certain cavities must be provided in the area of the periphery, between the sealing washer and the cap.

In all cases, certain cavities are provided between the sealing washer and the cap. It has emerged that residues of liquid can still reach these cavities, so that there is a danger of microbial impurity (germs). Thus, there is also the risk that microbial impurities can consequently reach the inside of the container, which is to be avoided from the point of view of sterility of the cleaned and disinfected contact lenses, in order to protect the contact lens wearer.

The problem is therefore to propose a contact lens container of the afore-mentioned kind, in which the risk of such microbial impurity of the contact lenses can at least be very greatly reduced, and which is simple to manufacture from a technical point of view.

This problem is solved by a contact lens container according to the invention, as is defined by the features of the independent patent claim. Further advantageous developments of the contact lens container according to the invention can be seen from the features of the dependent patent claims.

Owing to the fact that the sealing washer is equipped with a sealing lip at its border to the side wall of the cap—the lip being designed such that, when the sealing washer is deformed into the cavity, a water-tight seal is ensured with the side wall of the cap—when the sealing washer is deformed, no residues of liquid can reach into the cavity between the bottom of the cap and the sealing washer and accumulate there, and therefore also no microbial impurities can build up there, which might then reach the inside of the container. It is advantageous if the sealing lip is provided at the end of the sealing washer facing the container, since then the seal with the side wall is made as near as possible to the contact area with the liquid.

A sealing washer made of plastic with a modulus of elasticity (in tension) of ca. 200 $N/mm^2$ (test requirements ISO 527, DIN 53 457) is particularly suitable, especially a sealing washer made of a low density polyethylene (LDPE), however, basically other liquid- and gas-impermeable plastics may also be considered, which can be reversibly deformed in a similar way to a low density polyethylene (LDPE) of this kind, and which effect a similar or even greater extent of tightness between the sealing washer and the side wall of the cap.

It is also advantageous for the thread to have only a few, preferably one to two, turns for screwing the cap on and off. Then, the effort required to screw the cap on and off is only small, which increases handling comfort.

In a further advantageous embodiment, a contact lens holder is provided, which can be fixed to the cap. At its end projecting into the container, there are two convex bearing surfaces, as well as two concave baskets, which are pivotable about a pivot axis. The baskets each include webs, between which passages are provided for the cleaning and/or disinfecting liquid. The surface of the convex bearing surfaces is substantially larger than the surface of the webs of the concave baskets. This has the advantage that, when the baskets are opened, in the vast majority of cases, owing to the greater adhesion, the contact lens rests on the convex bearing surface, from which it can be more easily removed than from the concave baskets. The convex bearing surfaces may be preferably shaped as ribbed holohedrons.

It is also advantageous if, at the end of the respective basket facing away from the pivot axis, a distinct lug is provided for gripping and pivoting the concave basket. This simplifies opening and closing of the respective basket and thus increases handling comfort.

Finally, it is advantageous if a symbol is provided on the lug of at least one basket, the symbol being intended to identify the basket as that of a particular contact lens, e.g. the left contact lens. This simplifies the organizing of the right and left contact lens, which can be additionally supported by giving different colours to the baskets. A symbol can be, for example a raised letter "L" on the lug of the basket for the left contact lens, so that even if there is poor light in the surroundings, the respective contact lens can be sufficiently recognised and organized.

Figure 2:
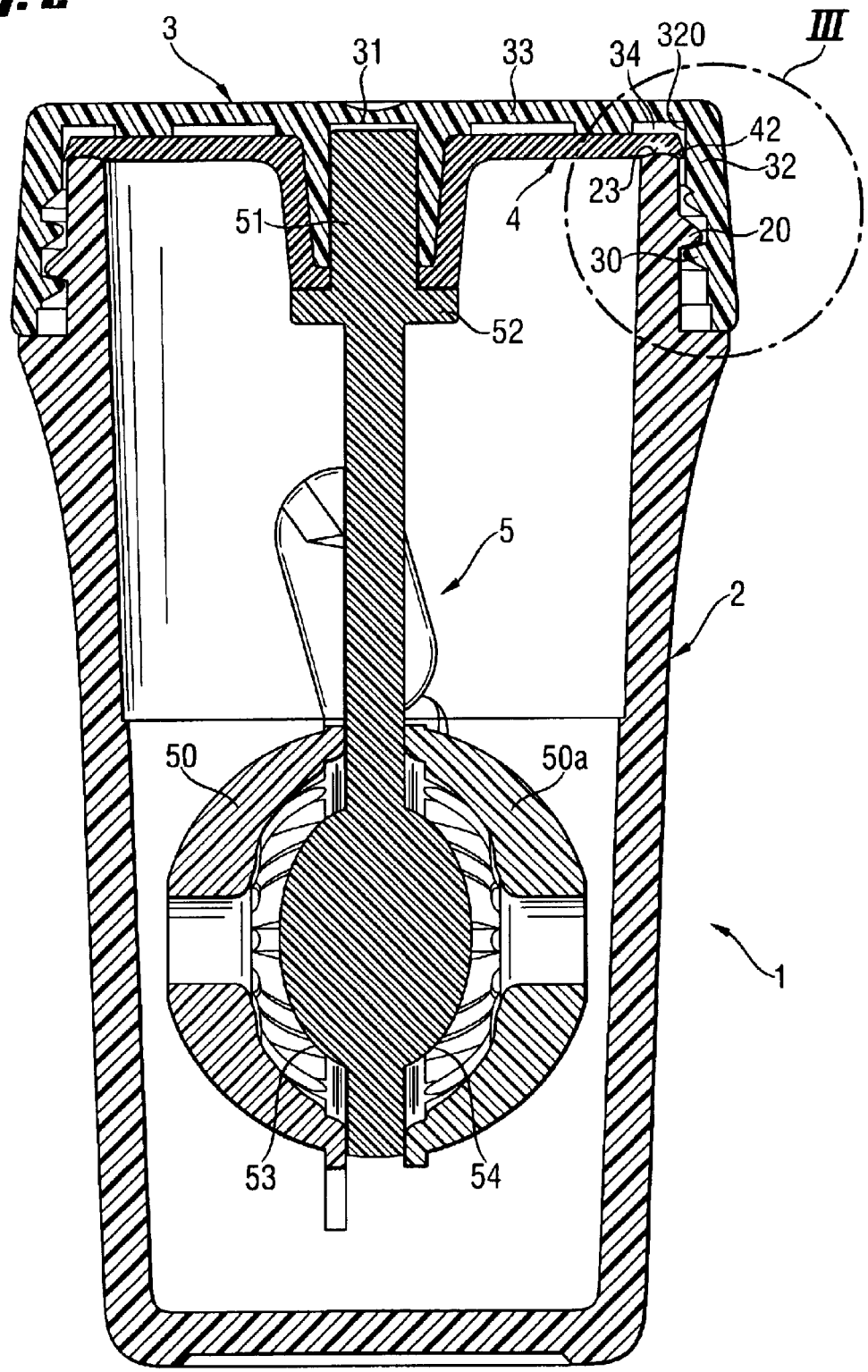
Figure 3:
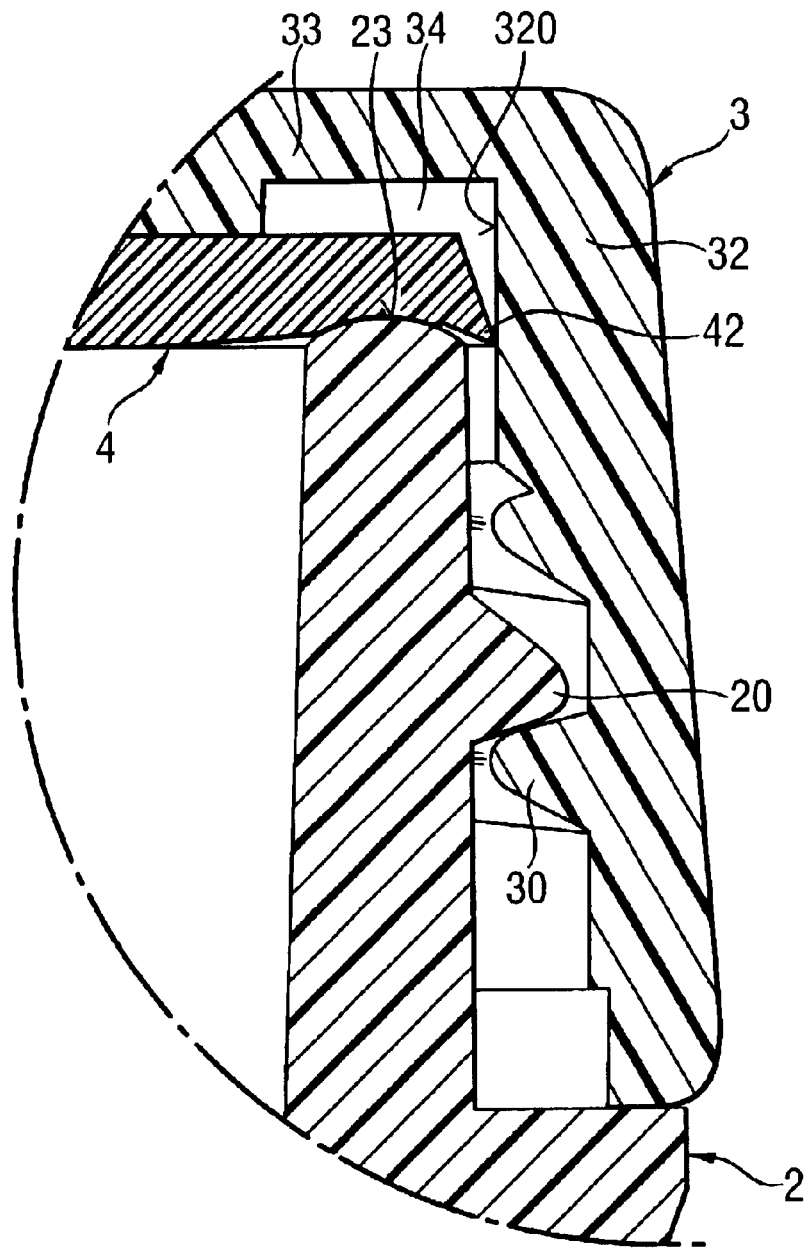
Figure 4:
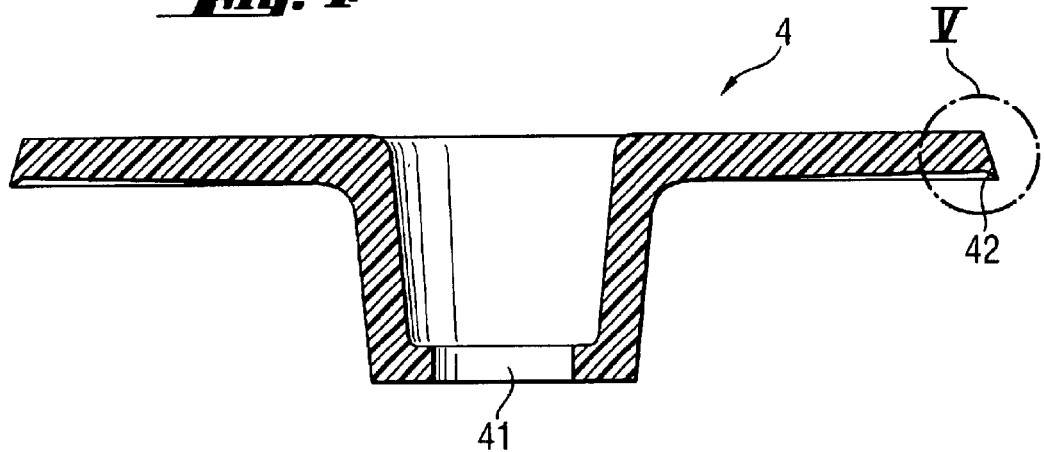
Figure 5:
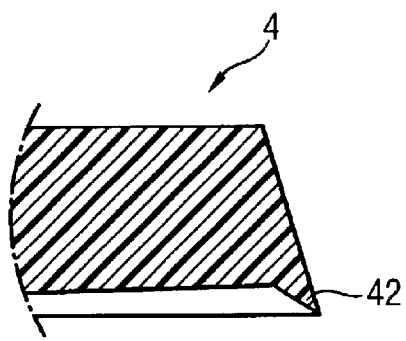
Figure 6:
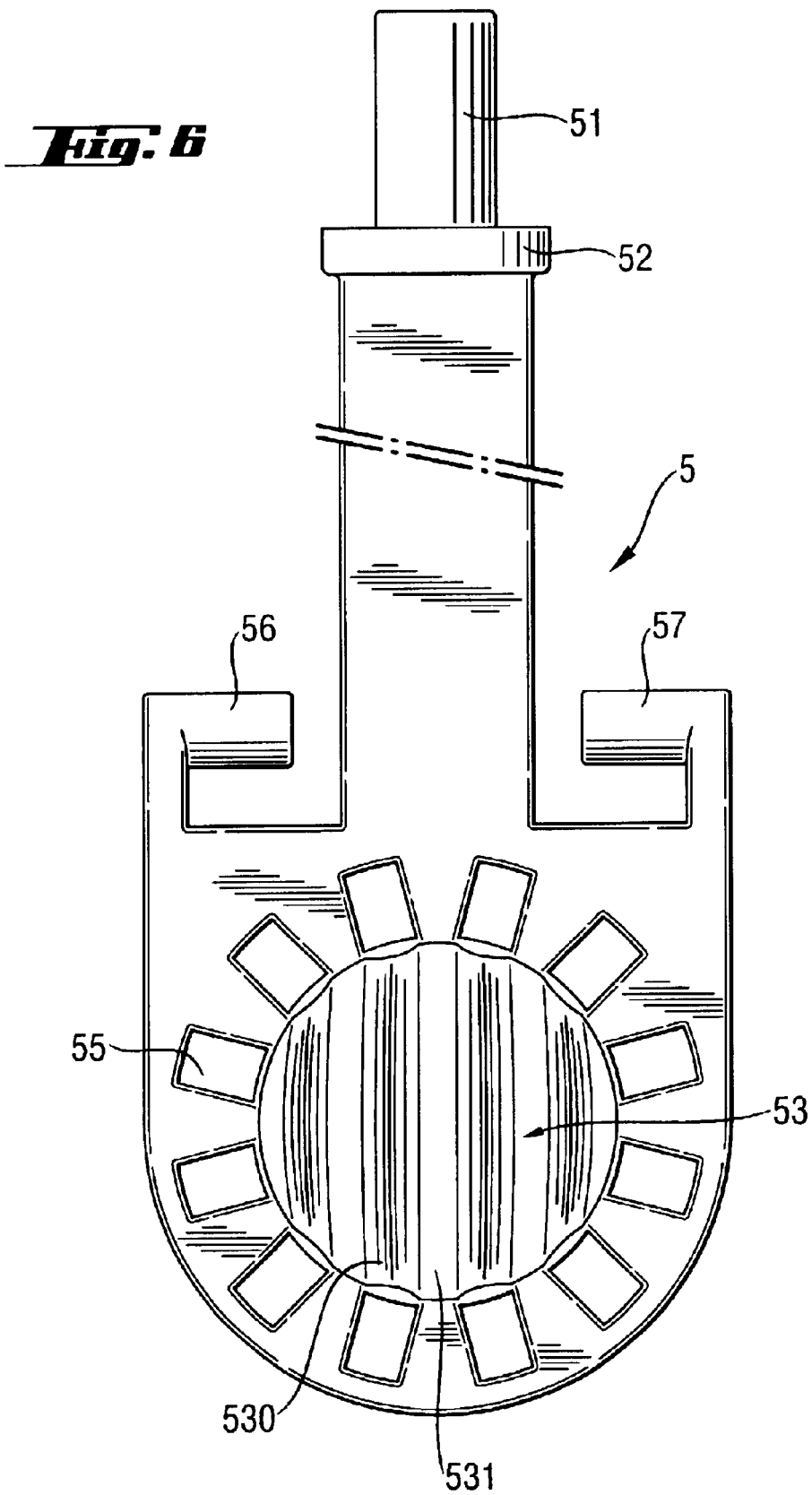
Figure 7:
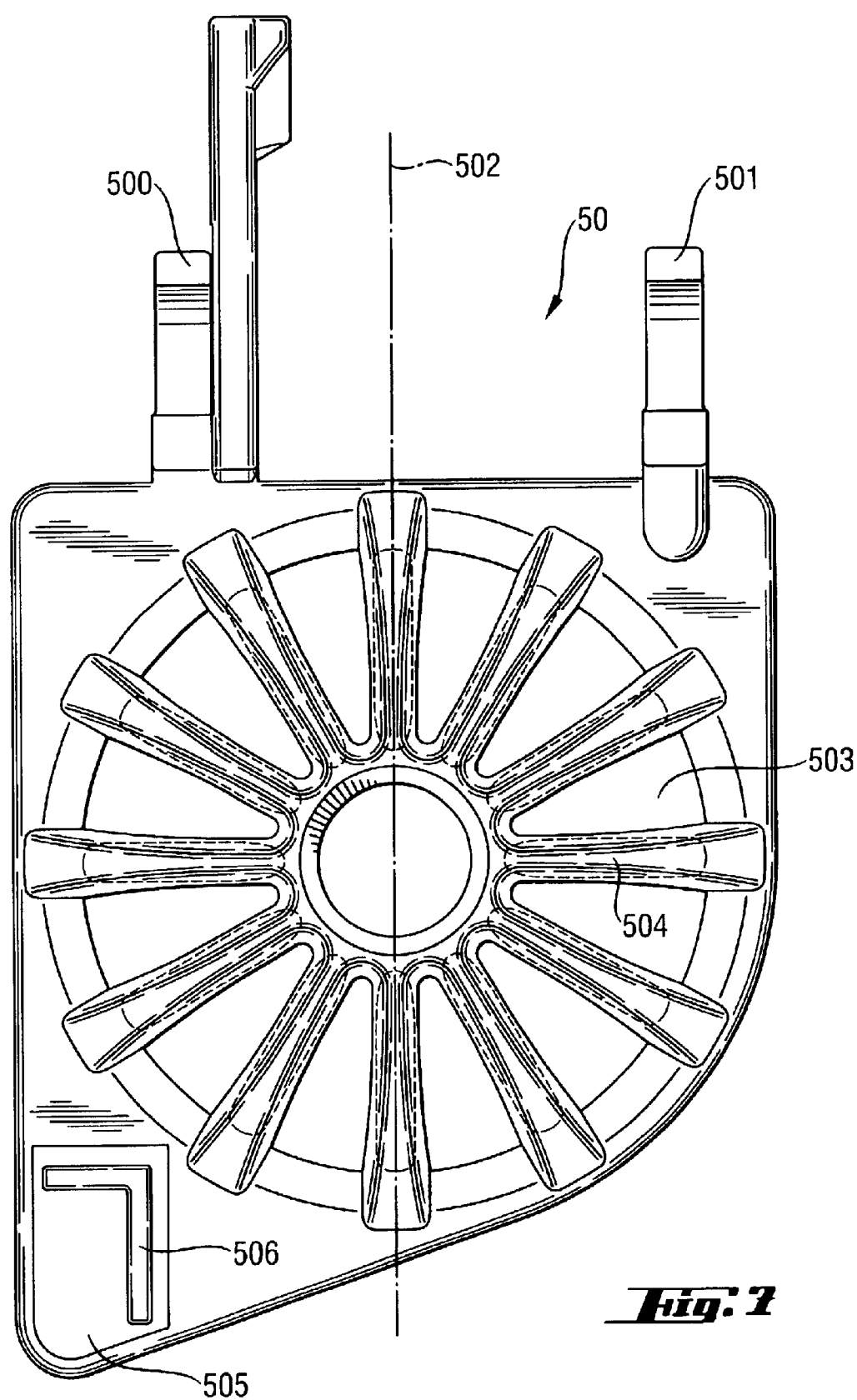

Further advantageous developments can be seen from the following description of advantageous embodiments in the drawings. These show:

FIG. 1 an embodiment of a contact lens container according to the invention with its components in a longitudinal section in an exploded illustration, FIG. 2 the embodiment of the contact lens container of FIG. 1 in assembled state, FIG. 3 section III of FIG. 2 in enlarged illustration, FIG. 4 the sealing washer of the embodiment of the contact lens container of FIG. 1 in enlarged illustration, FIG. 5 section V of FIG. 4 in enlarged illustration, FIG. 6 a plan view of the contact lens holder of the embodiment of the contact lens container from FIG. 1 and FIG. 7 a plan view of a basket of the embodiment of the contact lens container from FIG. 1.

FIG. 1 shows an embodiment of a contact lens container according to the invention (hereinafter simplified by calling it a contact lens container) with its components in an exploded view. The contact lens container 1 (shown in assembled form in FIG. 2) comprises in FIG. 1 a container 2 with an external thread 20, as well as a cap 3 with an internal thread 30, which can be made to engage with the external thread 20 of the container 2 by screwing the cap 3 onto the container 2. A centrally positioned holding fixture 31 for a contact lens holder 5 is provided in the cap 3. A sealing washer 4 may be introduced in the cap 3. The sealing washer 4 has a central opening 41, through which the proximal end 51 of the contact lens holder 5 can be placed. Thus, the contact lens holder 5 can be inserted through the central opening 41 of the sealing washer 4 into the holding fixture 31 of the cap 3. Two baskets 50 and 50a are pivotally connected to the contact lens holder 5.

FIG. 2 shows the contact lens container 1, which was illustrated in exploded view in FIG. 1, in the assembled state. The sealing washer 4 has been inserted into the cap 3, and the proximal end 51 of the contact lens holder 5 has been inserted through the central opening 41 of the sealing washer 4 into the holding fixture 31 of the cap 3. The contact lens holder 5 can be fixed to the holding fixture 31 either by a press fit (that is by friction) or this might also take place for example by a releasable snap fit. The central opening 41 of the sealing washer 4 is of a dimension such that—when the contact lens holder 5 is pushed through the opening 41—the surface of the sealing washer 4 facing radially inwards onto the corresponding outer surface of the proximal end 51 of the contact lens holder 5 rests tightly against the outer surface of the proximal end 51 of the contact lens holder 5. When the contact lens holder 5 has been correctly inserted into the cap 3, the surrounding projection 52 on the contact lens holder 5 similarly lies against the sealing washer 4.

As is likewise seen from FIG. 2 or FIG. 3, the sealing washer 4 extends radially to the inner surface 320 of the side wall 32 of the cap 3. When the cap 3 is screwed on, the sealing washer 4 is enclosed between the bottom 33 of the cap and the container edge 23, so that the container 2 has a water-tight seal. In the area in which the sealing washer 4 is enclosed between the container edge 23 and the bottom 33 of the cap (i.e. on the radially outer end of the sealing washer 4), a cavity is provided in the bottom 33 of the cap, and is in the form of a radially circumferential groove 34.

During operation, when the hydrogen peroxide breaks down, excess pressure occurs in the container 2 due to the oxygen being formed. In this instance, the sealing washer 4 in particular in the area enclosed between the container edge 23 and the bottom 33 of the cap is deformed into the groove 34, so that the oxygen can reach through the small gap thus formed between the sealing washer 4 and the container edge 23 into the pitch of the threads which are not gas-tight. Consequently, the oxygen formed upon decomposition of the hydrogen peroxide can in this way escape from the inside of the container through the thread and out of the container 2.

The problem already depicted initially in the case of existing contact lens containers having such cleaning systems is that, when the sealing washer 4 is deformed into the cavity behind the sealing washer 4, in this case into the slot 34, residues of liquid can seep in and also microbial impurities can occur. Then, there is the danger that such impurities (e.g. germs) can continue to grow and also reach the inside of the container, which should be avoided.

FIG. 3 shows the section III from FIG. 2 in an enlarged illustration. Here can be seen, above all, the manner in which the sealing washer 4 is shaped in its outer region, i.e. where it is enclosed between the bottom 33 of the cap and the container edge 23. The non-deformed state of the sealing washer 4 is shown in FIG. 3. The sealing washer 4 is also illustrated again in FIG. 4 and the section V from FIG. 4 is shown again in an enlarged illustration in FIG. 5. It can be seen especially well from FIG. 3 and FIG. 5 that the sealing washer 4 at its border with the inner surface of the side wall 32 of the cap 3—when assembled—is provided with a sealing lip 42 at its end adjoining the container edge 23. The sealing lip 42 is of such a shape that when the sealing washer 4 is deformed—that is, when oxygen escapes during decomposition of the hydrogen peroxide—the sealing lip 42 nevertheless rests against the inner surface of the side wall, and also when the sealing washer 4 is further deformed, a water-tight seal is provided against the inner surface of the side wall 32 of the cap 3. Consequently, no liquids can reach the slot 34, and also microbial impurities cannot reach there.

The sealing washer 4 is preferably made of a low density polyethylene (LDPE) and has a modulus of elasticity (in tension) of ca. 200 N/mm² for a thickness of the sealing washer in the range of ca. 1 mm to 1.5 mm. In the region of the sealing lip 42, the sealing washer can have in particular a thickness of 1 mm, whereby the sealing lip 42 itself has an (axial) thickness of about 0.2 mm, so that the total thickness in this region is ca. 1.2 mm. The material used for the sealing washer 4 may be in particular polyethylene known under the name "Lupolen® 1810 H", which is available commercially from the company Basell Polyolefine GmbH, D-77694 Kehl, Germany, from which the sealing washer 4 is produced by injection. This material is acceptable for the field of application relating to contact lens cleaning and/or disinfecting. Basically, however, other materials may also be considered. The sealing washer 4 may preferably be already firmly fixed in the cap 3, so that it can no longer be removed from the cap 3 in the contact lens container to be supplied.

As can be further seen from FIG. 2 and also from FIG. 3, the thread for screwing the cap 3 on and off only has a few turns, preferably one or two turns. In the embodiment illustrated here, a little more than one whole turn is provided, which is quite sufficient to ensure safe seating of the cap 3 on the container 2 and a tight connection. Little effort is therefore required to screw the cap 3 on and off, because it is not necessary to make several turns.

FIG. 6 illustrates a view of the contact lens holder 5 in a plan view. The projection 52 already discussed above is joined to the proximal end 51 of the contact lens holder 5. The proximal end 51 of the contact lens holder 5 is inserted through the central opening 41 in the sealing washer 4 into the holding fixture 31 of the cap 3, until the surrounding projection 52 abuts the sealing washer 4 (see FIG. 2). At the distal end of the contact lens holder 5, i.e. at the end which, during operation, projects into the container 2 or into the hydrogen peroxide solution located therein, there are two convex bearing surfaces 53 and 54. Only bearing surface 53 can be seen in FIG. 6, as the other bearing surface 54 is on the side facing the other way. As illustrated, the bearing surfaces 53 and 54 are preferably shaped as ribbed holohedrons with ridges 530 and troughs 531.

Around these bearing surfaces 53 and 54, openings 55 are provided to allow the hydrogen peroxide solution to pass through and thus enable rinsing to take place. Prior to beginning the cleaning and/or disinfecting procedure, one contact lens is placed on each convex bearing surface 53 and 54, and subsequently a basket 50 or 50a is pivoted about the pivot axes 56 and 57 until it snaps onto the contact lens holder 5 and encloses the contact lens.

The baskets 50 and 50a may be shaped as illustrated for example in FIG. 7 in a plan view of one basket 50. In particular, two fasteners 500 and 501 can be seen, which may be suspended on the pivot axes 56 and 57, so that the baskets 50 and 50a can be pivoted about the pivot axes 56 and 57. As is seen in FIG. 7, the fasteners 500 and 501 are each provided at a different distance from the central plane 502, because in each case another basket has to be suspended from the other side, and the fasteners of one basket should not hinder the fasteners of the other basket. The baskets 50 and 50a are of concave shape (on the side facing the contact lens or facing the bearing surface 53 or 54). They have openings 503, between which webs 504 extend. Rinsing may take place through the openings 503, which means that during operation the hydrogen peroxide solution can be circulated again and again, so that "fresh" hydrogen peroxide solution can continuously come into contact with the contact lenses.

As already mentioned above, the bearing surfaces 53 and 54 are preferably shaped as ribbed holohedrons, but this does not have to be the case. Basically, it is preferable for the surface of the convex bearing surfaces 53 and 54 to be greater than the surface of the webs of the concave baskets. This has the advantage that, when the baskets are opened after the cleaning and/or disinfecting procedure, the contact lens in the very great majority of cases remains on the convex bearing surface 53 or 54 (greater adhesion), from where it can be removed more simply than from the baskets 50 or 50a.

Finally, a distinct lug 505 is provided on each of the baskets 50 and 50a at the ends facing away from the pivot axes 56 and 57, by which the basket can be gripped and can be pivoted about the pivot axes 56 and 57. A symbol 506 can be provided on this lug 505, and in this case is in the form of a raised letter "L", so that the basket can be identified as being for the left contact lens. On the lug of the other basket, which is likewise arranged on the distal end, but on the other lateral end, a symbol may similarly be provided or also not provided. If at least one basket is provided with such a symbol, it is possible to clearly identify the basket for the left contact lens or for the right contact lens. Additionally, or also alternatively, it is also preferable for the baskets to be of different colours, in order to simplify identification of the basket for the left or right contact lens.

What we claim is:

1. A contact lens container, comprising: a liquid container for receiving a cleaning and/or disinfecting liquid, a cap, and a sealing washer, wherein the liquid container has an opening end with an external thread, wherein the cap has a bottom, a side wall surrounding the bottom, and an internal thread on the side wall, wherein the bottom includes a radially circumferential groove near the side wall, wherein the sealing washer includes a circumferential sealing lip located at its peripheral edge and is made of a water-tight and gas-tight material, wherein the sealing washer is arranged against the bottom of the cap and extends to the side wall of the cap with the sealing lip resting against the side wall, so that there is a first water-tight seal between the sealing washer and the side wall and a cavity formed between the circumferential groove and the the sealing washer, wherein a second water-tight seal is formed between the opening end of the liquid container and the sealing washer when the cap is screwed on to the container through engagement of the external and internal threads, wherein the second water-tight seal can be broken by excess pressure in the container which forces a portion of the sealing washer to be deformed into the cavity and thereby let gas escape from the inside of the container through the threads out of the container, wherein the sealing lip has a shape that, when the sealing washer is deformed into the cavity by the excessive pressure, the sealing lip remains resting against the side wall to ensure the first water-tight seal between the sealing washer and the side wall of the cap.

2. Contact lens container according to claim 1, wherein the sealing lip has a wedge shape.

3. Contact lens container according to claim 1, in which the sealing washer is made of a plastic having a modulus of elasticity in the region of about 200 N/mm$^2$.

4. Contact lens container according to claim 1, wherein the external thread and internal thread for screwing the cap on and off each have only a few turns.

5. Contact lens container according to claim 4, further comprising a contact lens holder which can be fixed to the cap, the end of the holder projecting into the container having two convex bearing surfaces, as well as two concave baskets which can be pivoted about a pivot axis, the baskets each having webs, between which outlets are provided for the cleaning and/or disinfecting liquid, whereby the surface of the convex bearing surfaces is substantially greater than the surface of the webs of the concave baskets.

6. Contact lens container according to claim 1, further comprising a contact lens holder which can be fixed to the cap, the end of the holder projecting into the container having two convex bearing surfaces, as well as two concave baskets which can be pivoted about a pivot axis, the baskets each having webs, between which outlets are provided for the cleaning and/or disinfecting liquid, whereby the surface of the convex bearing surfaces is substantially greater than the surface of the webs of the concave baskets.

7. Contact lens container according to claim 6, in which the convex bearing surfaces are shaped as ribbed holohedrons.

8. Contact lens container according to one of claim 7, in which a distinct lug for gripping and pivoting the concave basket is provided at the end of each concave basket facing away from the pivot axis.

9. Contact lens container according to one of claim 6, in which a distinct lug for gripping and pivoting the concave basket is provided at the end of each concave basket facing away from the pivot axis.

10. Contact lens container according to claim 9, characterised in that a symbol is provided on the lug of at least one basket, the symbol being intended to identify the basket as that of a particular contact lens, e.g. the left contact lens.

11. Contact lens container according to claim 2, wherein the sealing washer is made of a plastic having a modulus of elasticity in the region of about 200 N/mm$^2$.

12. Contact lens container according to claim 2, wherein the external thread and internal thread for screwing the cap on and off each have only a few turns.

13. Contact lens container according to claim 2, further comprising a contact lens holder which can be fixed to the cap, the end of the holder projecting into the container having two convex bearing surfaces, as well as two concave baskets which can be pivoted about a pivot axis, the baskets each having webs, between which outlets are provided for the cleaning and/or disinfecting liquid, whereby the surface of the convex bearing surfaces is substantially greater than the surface of the webs of the concave baskets.

14. Contact lens container according to claim 3, wherein the external thread and internal thread for screwing the cap on and off each have only a few turns.

15. Contact lens container according to claim 3, further comprising a contact lens holder which can be fixed to the cap, the end of the holder projecting into the container having two convex bearing surfaces, as well as two concave baskets which can be pivoted about a pivot axis, the baskets each having webs, between which outlets are provided for the cleaning and/or disinfecting liquid, whereby the surface of the convex bearing surfaces is substantially greater than the surface of the webs of the concave baskets.

* * * * *